Nov. 28, 1950 E. STARK Plant Pat. 995
PLUM TREE
Filed Aug. 14, 1948
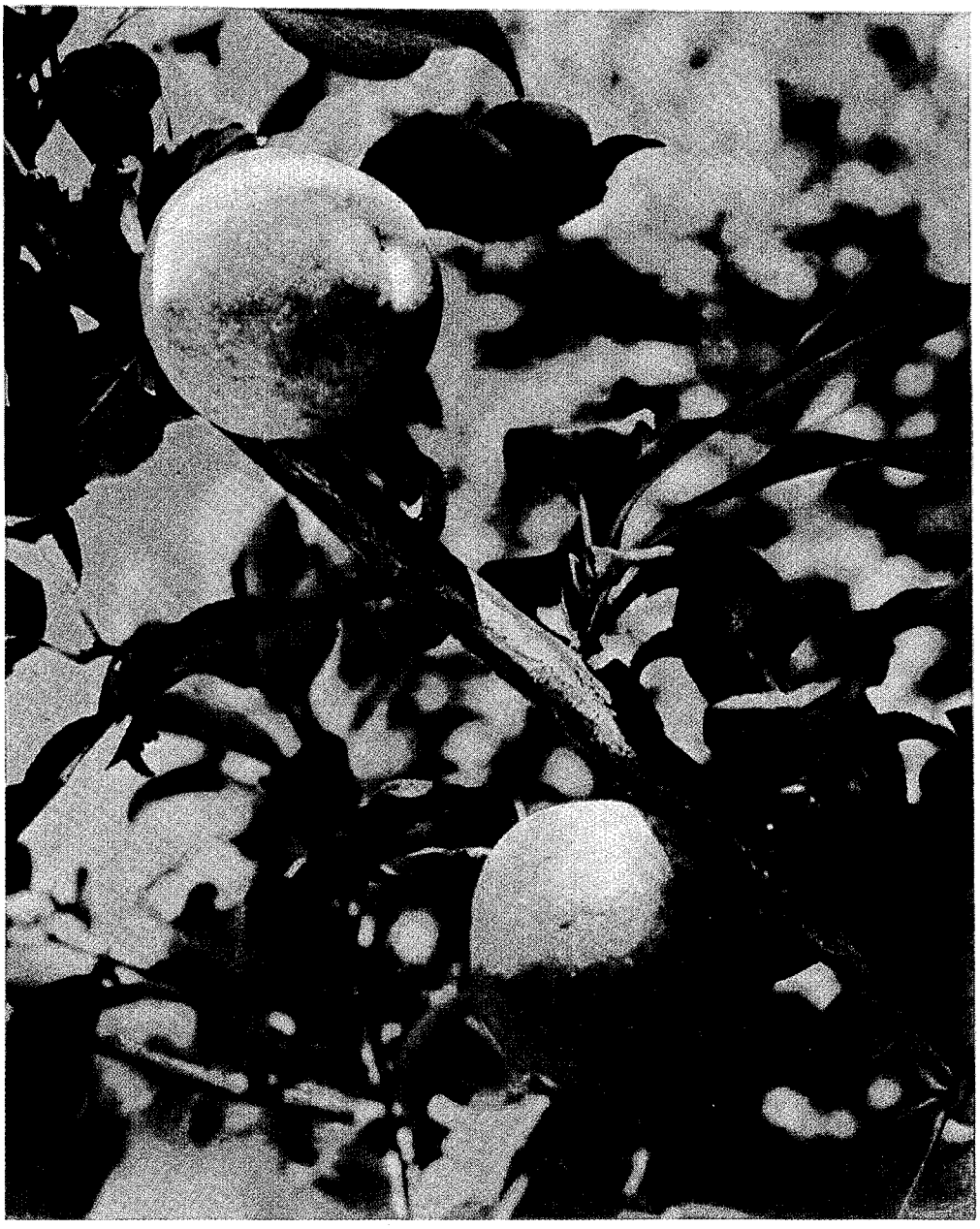
INVENTOR
Elmer Stark
BY Fleher and Swain
ATTORNEYS Patented Nov. 28, 1950

Plant Pat. 995

UNITED STATES PATENT OFFICE

995

PLUM TREE

Elmer Stark, Di Giorgio, Calif., assignor to Di Giorgio Fruit Corporation, San Francisco, Calif., a corporation of California Application August 14, 1948, Serial No. 44,350

1 Claim. (Cl. 47—62)

This invention relates to a new and distinct variety of plum tree.

One of the objects in the creation of the present variety of plum was to improve upon the Santa Rosa plum which, while it has many of the characteristics which are desirable from a commercial standpoint, does have certain very obvious disadvantages. For example, it was one of my objects to create a plum which was exceedingly resistant to both insects and diseases. Furthermore, I wished to provide a plum which matured considerably earlier than the Santa Rosa.

Not only has the present plum the foregoing desirable characteristics, but it has proved to be larger in size than the Santa Rosa and to have a more pleasing color.

The attached drawing and specification show the distinctions and characteristics of the new variety of plum which has been asexually reproduced.

In describing the tree and fruit I shall refer specifically to the Santa Rosa plum inasmuch as the same is a well known and well established variety, and all references thereto will be clearly understood by those skilled in horticultural sciences. The tree and fruit have been asexually reproduced at the nursery at Di Giorgio Farms, Di Giorgio, California.

The tree, generally speaking, is larger than the Santa Rosa and, like the Santa Rosa, is open. The tree is rapid growing, hardy and spreading. The trunk is stocky and shaggy. The branches, of which there are many, are thick and are similar in color to the Santa Rosa.

The leaves are slightly longer and broader than the Santa Rosa although of the same general shape, that is, pointed and broad. They are of a deeper green than the Santa Rosa. The margins of the leaves are serrate.

The petiole is shorter than the Santa Rosa yet sturdier and heavier.

The flower, which lasts from ten to twelve days, is white and slightly larger than the Santa Rosa and blooms four or five days later than the Santa Rosa. The blossom has an open calyx.

The fruit, which matures four or five days earlier than the Santa Rosa, is approximately twice the size of the Santa Rosa having an axial diameter slightly less than the Santa Rosa but a transverse diameter considerably greater. The fruit is regular in form and is nearly round, its diameter being substantially uniform with the exception, however, that the axial diameter may be the longer by a fraction of an inch. The cavity is symmetrical and is both deeper and wider than the Santa Rosa, with the rib running into the cavity clear from the stem to the tip of the fruit.

The basin is furrowed and pronounced whereas the Santa Rosa is smooth. Generally speaking, the basin is deep and wide, furrowed and symmetrical.

The stem of the fruit is shorter than the Santa Rosa and is sturdier and heavier.

The skin of the plum is thick, smooth and clean and of a slightly darker green than the Santa Rosa during growing period and when ripe it is red and striped and may be considered to be substantially the same color as the Santa Rosa although slightly darker.

The flesh of the fruit is moist and of a slightly coarser texture than the Santa Rosa. The flavor and aroma of the fruit is generally the same as the Santa Rosa.

The fruit is the cling type. The seeds are slightly longer than the Santa Rosa and considerably broader and are more irregular than the Santa Rosa.

The plum is particularly adaptable for market uses since it has excellent keeping qualities, has a pleasing aroma and taste and is attractive to the eye.

The fruit is further attractive commercially in that it is extremely resistant to both insects and diseases. For example, it has been noted that this fruit has a relatively high resistance to spoilage both while on the tree and during the packing and shipping operations.

I claim:

The plum tree herein described and shown characterized particularly by the larger size and round shape of its fruit.

ELMER STARK.

REFERENCES CITED

The following references are of record in the file of this patent:

UNITED STATES PATENTS

| Number | Name | Date |
|---|---|---|
| Pl. Pt. 721 | Howard | Dec. 31, 1946 |
| Pl. Pt. 793 | Kellogg | Mar. 23, 1948 |